United States Patent
Aoyama

(10) Patent No.: US 7,892,757 B2
(45) Date of Patent: Feb. 22, 2011

(54) IMMUNOCHEMICAL DETERMINATION METHOD AND DETERMINATION REAGENT FOR CYTOCHROME C

(75) Inventor: Muneo Aoyama, Ibaraki (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 536 days.

(21) Appl. No.: 11/911,612

(22) PCT Filed: Apr. 17, 2006

(86) PCT No.: PCT/JP2006/308079

§ 371 (c)(1),
(2), (4) Date: Oct. 15, 2007

(87) PCT Pub. No.: WO2006/112445

PCT Pub. Date: Oct. 26, 2006

(65) Prior Publication Data

US 2009/0075290 A1 Mar. 19, 2009

(30) Foreign Application Priority Data

Apr. 15, 2005 (JP) .............................. 2005-118192

(51) Int. Cl.
*G01N 33/53* (2006.01)
(52) U.S. Cl. ........................ 435/7.1; 435/7.9; 435/7.91; 435/7.95; 435/970; 435/975; 435/7.94

(58) Field of Classification Search .................. 435/7.1, 435/7.9, 7.91, 7.95, 970, 975
See application file for complete search history.

(56) References Cited

U.S. PATENT DOCUMENTS

| 2002/0192712 A1* | 12/2002 | Endo et al. .................. 435/7.1 |
| 2006/0183176 A1* | 8/2006 | Endo et al. .................. 435/7.93 |

FOREIGN PATENT DOCUMENTS

| EP | 1 229 328 A1 | 8/2002 |
| JP | 3 257367 | 11/1991 |
| JP | 2003 28860 | 1/2003 |
| WO | 98 02579 | 1/1998 |
| WO | 01 35093 | 5/2001 |

OTHER PUBLICATIONS

Paulo S. Ribeiro, et al., "Hepatocyte Apoptosis, Expression of Death Receptors, and Activation of NFκB in the Liver of Nonalcoholic and Alcoholic Steatohepatitis Patients", American Journal of Gastroenterology, 2004, 99: pp. 1708-1717.

* cited by examiner

*Primary Examiner*—Bao-Thuy L Nguyen
(74) *Attorney, Agent, or Firm*—Oblon, Spivak, McCleland, Maier & Neustadt, L.L.P.

(57) ABSTRACT

An immunochemical method for the accurate measurement of the quantity of cytochrome c in a body fluid, in particular, blood, and a kit for the measurement. The quantity of cytochrome c can be measured accurately without being affected by any interfering substrate by reacting an antibody with cytochrome c in a buffer solution in an acidic range.

11 Claims, 1 Drawing Sheet

IMMUNOCHEMICAL DETERMINATION METHOD AND DETERMINATION REAGENT FOR CYTOCHROME C

CROSS-REFERENCE TO RELATED APPLICATIONS

This application is a 371 of PCT/JP06/308079 filed Apr. 17, 2006 and claims the benefit of JP 2005 118192 filed Apr. 15, 2005.

TECHNICAL FIELD

The present invention relates to an immunochemical method and measurement kit for accurately measuring cytochrome c in a body fluid, in particular, blood.

BACKGROUND ART

Cytochrome c has long been studied as a protein involved in the electron transport system, and then as an apoptosis-related protein in recent years, and methods for immunochemically measuring intracellular cytochrome c concentrations or blood cytochrome c concentrations are known (Non-patent document 1). Further, since the blood cytochrome c concentration is known to serve as an index of apoptosis occurring in the body (Non-patent document 2 and Patent documents 1 and 2), use thereof as a diagnostic agent for many diseases is being expected.

It has been confirmed that when cytochrome c in a body fluid, in particular, blood, is measured by using conventional cytochrome c measurement methods and measurement kits, measured values reflect amounts of cytochrome c, and there is no problem in investigation of apoptosis occurring in the body. However, so far, whether the measured values accurately reflect the amounts of cytochrome c in body fluids has not been verified, and a measurement method and measurement kit for obtaining an accurate measured value of cytochrome c in a body fluid have been desired.

Patent document 1: WO01/35093
Patent document 2: Japanese Patent Laid-open (Kokai) No. 2003-028860
Non-patent document 1: Andrea Renz, et al., Rapid extracellular release of cytochrome c is specific for apoptosis and markers cell death in vivo, BLOOD, 98(5) 1542-1548, 2001
Non-patent document 2: Z. BEN-ARI, et al., Circulating soluble cytochrome c in liver disease as marker of apoptosis, Journal of Internal Medicine, 254, 168-175, 2003

DISCLOSURE OF THE INVENTION

An object of the present invention is to provide an immunochemical method and measurement kit for accurately measuring cytochrome c in a body fluid, in particular, blood.

The inventors of the present invention performed a recovery test according to a conventional sandwich method, in which a known amount of cytochrome c was added to serum, and the amount was measured. While they found that a measured value showing whether the addition amount is large or small could be obtained, a measured value accurately reflecting an addition amount could not be obtained.

As a result of investigation for various measurement conditions, they found that an accurate measured value of cytochrome c in serum could be obtained by making a pH of a buffer solution used for the reaction of cytochrome c and an anti-cytochrome c antibody to be in an acidic range, and thus accomplished the present invention.

That is, the present invention relates to the followings.
[1] A method for immunochemically measuring cytochrome c in a body fluid, which comprises reacting an antibody and cytochrome c in a buffer solution in an acidic range.
[2] The method according to [1], wherein the acidic range is a range of pH 3.5 to 5.0.
[3] The method according to [1] or [2], wherein the body fluid is blood.
[4] A kit for immunochemically measuring cytochrome c in a body fluid, which is adapted for reaction of an antibody and cytochrome c in a buffer solution in an acidic range.
[5] The kit according to [4], wherein the acidic range is a range of pH 3.5 to 5.0.
[6] The kit according to [4] or [5], which comprises at least (1) an antibody that reacts with cytochrome c, and (2) a buffer solution that allows the reaction in an acidic range.
[7] The kit according to [6], wherein the antibody that reacts with cytochrome c is an immobilized antibody and/or a labeled antibody.
[8] The kit according to any one of [4] to [7], wherein the body fluid is blood.

The inventors of the present invention further revealed based on a proteome technique using mass spectrometry that interference substances in human serum, which inhibit accurate quantification of cytochrome c, were highly acidic proteins such as $\alpha 1$-acid glycoprotein and $\alpha 1$-antitrypsin.

According to the present invention, it was revealed that highly acidic proteins in serum influenced binding of cytochrome c and an antibody, and that the influence was eliminated by reacting cytochrome c and an antibody in an acidic range, and other methods for suppressing the influence of the highly acidic proteins on the reaction between cytochrome c and an antibody, for example, a method of adjusting the salt concentration of the reaction mixture, are also encompassed by the present invention.

According to the present invention, an immunochemical measurement method for accurately measuring cytochrome c in a body fluid, in particular, blood, is established, and reliability of a measured value of cytochrome c is increased.

BEST MODE FOR CARRYING OUT THE INVENTION

Figure 1:
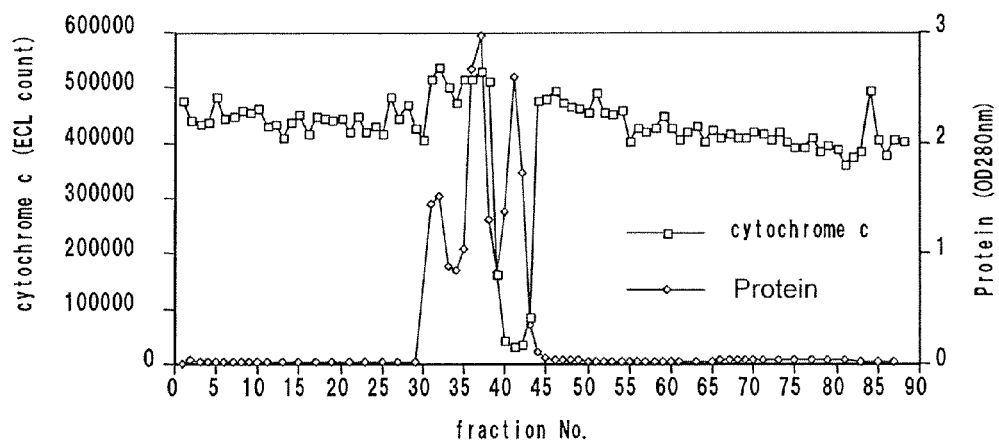
FIG. 1 shows interference activities of fractions obtained by subjecting human serum to gel filtration, on the measurement of cytochrome c.

The subject matter of the present invention is an immunochemical measurement method for measuring amount of cytochrome c in a body fluid, in particular, blood, which comprises reacting an anti-cytochrome c antibody and cytochrome c in an acidic range to attenuate influence of interference substances in the body fluid, which influence the binding of the anti-cytochrome c antibody and cytochrome c, so that an accurate measured value of cytochrome c can be obtained.

Therefore, the term "acidic range" used in the present specification means a pH range in which influence of interference substances in the body fluid, which influence the binding of an antibody and cytochrome c, is attenuated.

Although the influence of interference substances can be reduced by lowering pH, the binding between the antibody and cytochrome c is also weakened at the same time. Therefore, pH for the immunochemical measurement according to the present invention may be determined to be a pH that satisfies the following conditions 1 and 2.

1. Measurement sensitivity enabling quantification of 10 ng/mL, preferably 1 ng/mL, of cytochrome c in a buffer solution can be afforded.
2. A recovery rate of 70% or higher, preferably 80% or higher, more preferably 90% or higher, can be afforded in a spiked recovery test in the presence of a body fluid.

Since the effect of pH on binding of an antibody and cytochrome c varies depending on the antibody used, pH used in the immunochemical measurement method can be determined to be a pH optimal for each particular antibody. The pH is preferably 7 or lower, more preferably 3 to 6, still more preferably 3.5 to 5, even more preferably 3.5 to 4.5.

Hereafter, a method for determining pH used for the immunochemical measurement of the present invention will be shown specifically. However, the method for determining pH is not limited to this example.

1. Influence of pH on Measurement Sensitivity

Cytochrome c is diluted to 1 to 1000 ng/mL in a buffer solution of pH 3 to 7.5 containing appropriate proteins such as BSA, appropriate salts such as NaCl, appropriate surfactants and so forth as required.

When the immunochemical measurement method is a two-step sandwich method, the diluted cytochrome c and an immobilized anti-cytochrome c antibody are reacted, after washing, a labeled anti-cytochrome c antibody is added, and the labeling substance is detected based on an activity corresponding to the labeling substance, such as radioactivity in the case of radioactive labeling and enzymatic activity in the case of enzyme labeling.

Further, when the immunochemical measurement method is a one-step sandwich method, the diluted cytochrome c, an immobilized anti-cytochrome c antibody, and a labeled anti-cytochrome c antibody are mixed and reacted, and the labeling substance is detected based on an activity corresponding to the labeling substance, such as radioactivity in the case of radioactive labeling and enzymatic activity in the case of enzyme labeling.

If a signal obtained from a specimen containing 10 ng/mL, preferably 1 ng/mL, of cytochrome c is sufficiently stronger than that of a specimen not containing cytochrome c but comprising a buffer solution alone, the used pH can be mentioned as a candidate pH of the buffer solution used for the immunochemical measurement method.

2. Influence of pH on Spiked Recovery

When cytochrome c in a body fluid corresponding to a specimen used in the immunochemical measurement method, for example, serum, is measured, a known amount of cytochrome c is added to the serum. The amounts of cytochrome c in serum to which cytochrome c is added and serum to which cytochrome c is not added are measured by the immunochemical method, and the ratio of the measured value to the theoretical value is obtained as a recovery rate.

If the addition amount of cytochrome c is represented by A, the measured value of cytochrome c in serum to which cytochrome c is not added is represented by B, and the measured value of cytochrome c in serum to which cytochrome c is added is represented by C, the recovery rate can be calculated in accordance with either of the following equations:

$$\text{Measured value (C)/Theoretical value (weighted average of A and B)} \quad (1)$$

$$\text{Increase in measured value by addition of cytochrome c (C−B)/Addition amount (A)} \quad (2)$$

If the recovery rate is 70% is higher, preferably 80% or higher, more preferably 90% or higher, the pH can be mentioned as a candidate pH of a buffer solution used for the immunochemical measurement method.

The pH of the buffer solution used for the immunochemical measurement method is determined taking 1. influence of pH on measurement sensitivity, and 2. influence of pH on spiked recovery, into account.

Further, in the immunochemical measurement of cytochrome c according to the present invention, a method of using a buffer solution in an acidic range is effective not only for the first reaction in which an immobilized antibody and cytochrome c in a specimen are reacted, but also for the second reaction (the step of reacting cytochrome c and a labeled antibody) when the interference substances cannot be completely removed in the first reaction.

The method of the present invention is not limited to a method of using a buffer solution in an acidic for the first reaction.

The buffer solution used for the reaction of cytochrome c in blood and an antibody directed to cytochrome c in an acidic range is determined taking 1. influence of pH on measurement sensitivity and 2. influence of pH on spiked recovery mentioned above into account. Type of the buffer solution is not particularly limited so long as the buffer solution can be prepared to be in an acidic condition, and examples thereof include succinate buffer solution, citrate phosphate buffer solution and so forth.

The method of the present invention may be performed in the same manner as that of usual immunological methods for measuring amount of cytochrome c in a body fluid except that an anti-cytochrome c antibody and cytochrome c are reacted in an acidic range as described above.

The term "immunochemical method" used herein means a method for quantifying cytochrome c by using an antibody directed to cytochrome c. Examples of the immunochemical method include a wide variety of methods such as the competitive method in which cytochrome c is labeled, sandwich method in which the antibody is labeled, and latex bead method in which agglutination of antibody-coated beads is observed, and any types of methods using an antibody directed to cytochrome c falls within the scope of the method of the present invention. Type of the anti-cytochrome c antibody is not particularly limited so long as an antibody enabling detection of cytochrome c is chosen. It may be IgG, IgG $F(ab')_2$ fragment, or Fab fragment, and it may be either a monoclonal antibody or a polyclonal antibody. Further, the antibody may be an immobilized antibody or a labeled antibody. Various labeling methods are available, including labeling with a radioactive isotope, labeling with an electrochemiluminescent compound, fluorescence labeling, enzyme labeling, biotin labeling, and so forth, and the present invention is not limited by these examples. Methods for preparing antibodies and labeling methods are described in, for example, Lecture of Biochemical Experiments, Second series, Vol. 5, Research Methods for Immunobiochemistry (edited by The Japanese Biochemical Society and published by Tokyo Kagaku Dozin Co., Ltd.) or Lecture of New Biochemistry Experiments, Vol. 12, Molecular Immunology III (edited by The Japanese Biochemical Society and published by Tokyo Kagaku Dozin Co., Ltd.).

In the present specification, examples of the body fluid include blood, plasma, serum, cerebrospinal fluid, cord blood, urine, amniotic fluid, broncho-alveolar lavage fluid collected from living body and so forth. Among these, blood is preferred.

The method of the present invention is usually performed by reacting an anti-cytochrome c antibody and cytochrome c in a sample in an acidic range, and then detecting the reacted cytochrome c. The detection is preferably performed by, for example, a method of reacting a labeled secondary antibody after washing, and detecting cytochrome c by a detection method corresponding to the label. For example, when a biotin-labeled secondary antibody is used, an enzyme such as avidin-labeled peroxidase or alkaline phosphatase can be further reacted, and then cytochrome c can be detected by using a substrate of the enzyme on the basis of luminescence or color development. Further, an enzyme-labeled secondary antibody, fluorescence-labeled secondary antibody, ruthenium-labeled secondary antibody and so forth may also be used.

Examples of the immunochemical method for measuring cytochrome c include a method of using an anti-cytochrome c antibody labeled with a ruthenium complex prepared by the method described in the reference examples mentioned below.

The present invention also relates to a kit for immunochemically measuring cytochrome c in a body fluid. The kit of the present invention is a kit for reacting an anti-cytochrome c antibody and cytochrome c in a buffer solution in an acidic range. Examples thereof include a kit comprising an instruction describing that cytochrome c and an anti-cytochrome c antibody should be reacted under an acidic condition. Further, it may be a kit comprising a reaction buffer solution prepared to be acidic. The kit of the present invention may comprise a secondary antibody, standard cytochrome c solution, diluent, washing solution, substrate for detection and so forth, besides the anti-cytochrome c antibody.

The kit of the present invention usually comprises reagents for quantifying cytochrome c in a body fluid, in particular, blood, by using an antibody directed to cytochrome c (cytochrome c measurement reagents). For example, measurement reagents for measuring cytochrome c by a sandwich method as examples of the cytochrome c measurement reagents include, for example, 1) an anti-cytochrome c antibody-coated cup or an anti-cytochrome c antibody coated beads, and 2) a labeled anti-cytochrome c antibody, and preferably further include 3) a standard cytochrome c solution having a known concentration, 4) a diluent, and 5) a washing solution. Further, in the case of using enzyme labeling, the regents may include 6) a substrate for color development, and 7) a solution for terminating the reaction.

The measurement kit of the present invention preferably includes a buffer solution for reacting cytochrome c in blood and an antibody directed to cytochrome c in an acidic range.

The buffer solution included in the measurement kit of the present invention may be a buffer solution to be used for the reaction as it is or a buffer solution to be diluted before use. Further, it may be a buffer solution adjusted to have a pH in an acidic range suitable for the present invention by adding an acidic or alkaline solution in an appropriate volume, or a buffer solution attached with an instruction describing such pH adjustment.

EXAMPLES

The present invention will be explained more specifically with reference to the following examples. However, the scope of the present invention is not limited by these examples.

Reference Example 1

Purification of Anti-Cytochrome c IgG

Rabbits were immunized with rat cytochrome c (Sigma) to obtain anti-cytochrome c antiserum. Ammonium sulfate was added to the antiserum at a final concentration of 2 M, and the mixture was stirred at room temperature (20 to 30° C.) for 5 hours. The stirred solution was centrifuged at 10000 rpm for 30 minutes, the supernatant was discarded, a 0.1 M phosphate buffer solution (pH 7.2) was added to the precipitates to dissolve them, and then the solution was dialyzed against a 0.1 M phosphate buffer solution (pH 7.2).

The dialyzed solution was flown through a CNBr-Sepharose 4B (GE HEALTHCARE Biosciences) column bound with bovine cytochrome c (Sigma), the column was washed with a 0.01 M Tris-hydrochloride buffer solution (pH 7.5) containing 0.15 M NaCl, and then IgG was eluted with 0.1 M guanidine hydrochloride. The eluted IgG fraction was dialyzed against a 0.01 M Tris-hydrochloride buffer solution (pH 7.5) containing 0.15 M NaCl to obtain purified anti-cytochrome c IgG.

Reference Example 2

Preparation of Anti-cytochrome c IgG F(ab')$_2$ Polyclonal Antibody

The purified anti-cytochrome c IgG was dialyzed against a 0.1 M acetate buffer solution (pH 4.2). Pepsin (Sigma) was added thereto at a protein concentration ratio of 20:1, and the mixture was allowed to react at 37° C. for 16 hours. The reaction mixture was adjusted to pH 7.5 by addition of 1 N NaOH, and flown through a Sephacryl S-200 (GE HEALTHCARE Biosciences) column equilibrated with a 0.01 M Tris-hydrochloride buffer solution (pH 7.5) containing 0.15 M NaCl to perform gel filtration. The fractions of the first peak were collected and concentrated to obtain an anti-cytochrome c IgG F(ab')$_2$ polyclonal antibody.

Reference Example 3

Preparation of Anti-Cytochrome c Monoclonal Antibody

Human cytochrome c (R&D Systems) in an amount of 110 μg/100 μL and 55 μL of 2 mg/mL ovalbumin dissolved in a 65 mM phosphate buffer solution (pH 7.5) were mixed, to the mixture was added 42 μL of 1 mM glutaraldehyde diluted with a 65 mM phosphate buffer solution (pH 7.5), and the mixture was stirred at room temperature for 2 hours. Then, the mixture was dialyzed against 0.15 M NaCl at 4° C. for 48 hours, an adjuvant was prepared with equal amount of FCA, and 0.1 mL thereof was administered to the peritoneal cavities of BALB/C mice to immunize the mice. The immunization was performed in the same manner 3 times every 2 weeks. Two weeks after the third immunization, 50 μg/100 μL of human cytochrome c dissolved in physiological saline was given to the mice by intravenous injection from the caudal vein. Three days later, the spleens were removed from the mice, and spleen lymphocytes were fused with myeloma cell P3X63 Ag8U.1 according to the polyethylene glycol method in a conventional manner. Screening was performed by using human cytochrome c as an antigen to establish a hybridoma producing a monoclonal antibody directed to human cytochrome c (clones: 3G7 and 27G9).

The established hybridoma was cultured and proliferated in the S-Clone SF-B medium (Sanko Junyaku Co., Ltd.) and inoculated into the peritoneal cavities of BALB/C mice. After 1 week, ascites was collected. IgG was purified from the collected ascites by using protein A to obtain anti-cytochrome c antibodies (3G7 antibody and 27G9 antibody).

Reference Example 4

Preparation of Anti-Cytochrome c Antibody-Immobilized Beads

The anti-cytochrome c monoclonal antibody (clone: 2B5F8 (R&D Systems) or clone: 6H2.B4 (Becton Dickinson)) was dialyzed against a 0.1 M acetate buffer solution (pH 4.2) containing 0.15 M NaCl, and diluted with a 0.1 M acetate buffer solution (pH 4.2) containing 0.15 M NaCl to have an OD 280 nm of 0.56. The diluted antibody in a volume of 1.67 mL was mixed with 3.36 mL of beads (Dynabeads® M-450 Epoxy, Dynal) washed beforehand three times with 3 mL of a 0.1 M acetate buffer solution (pH 4.2) containing 0.15 M NaCl using a magnet, and the mixture was stirred at room temperature for 17 hours. Then, the beads were suspended in 3 mL of a blocking buffer solution (50 mM Tris-HCl, 1% BSA, 0.15 M NaCl, 0.1% $NaN_3$, pH 7.5), and the suspension was stirred at room temperature for 7 hours to block the beads. The concentration of the blocked beads was adjusted before use, and then the beads were used for the measurement.

Reference Example 5

Preparation of Ruthenium Complex-Labeled Anti-Cytochrome c Antibody

The anti-cytochrome c monoclonal antibody prepared in Reference Example 3 (3G7 antibody or 27G9 antibody) or the anti-cytochrome c IgG F(ab')$_2$ polyclonal antibody prepared in Reference Example 2 was dialyzed against PBS, and the antibody concentration was adjusted to be in the range of 0.5 to 2 mg/mL. To 1 mL of the antibody was added 12.2 μL of a ruthenium complex (ruthenium(II) tris(bipyridyl)-N-hydroxysuccinimide, IGEN Corp. USA) dissolved in dimethyl sulfoxide at a concentration of 10 mg/mL, and the mixture was stirred at room temperature for 30 minutes. Then, to the mixture was added 50 μL of 2 M glycine, and the mixture was stirred at room temperature for 10 minutes. The mixture was applied to a Sephadex G-25 (GE HEALTHCARE Biosciences) column (1.5 cm φ×30 cm) equilibrated beforehand with PBS-3 (10 mM potassium phosphate, 0.15 M NaCl, 0.05% $NaN_3$, pH 6.0) and eluted with PBS-3 to collect 1-mL fractions. The OD of each fraction was measured at 280 nm, and fractions of the first peak were collected to obtain an anti-cytochrome c antibody labeled with a ruthenium complex. The antibody concentration was measured by using Micro BCA Protein Assay Kit (PIERCE).

Reference Example 6

Preparation of Standard Human Cytochrome c Antigen

Standard cytochrome c antigens were prepared by diluting human cytochrome c (R&D Systems) with a 0.15 M sodium phosphate buffer solution (pH 7.4) containing 5% BSA, 0.15 M NaCl and 0.1% $NaN_3$ to 1000, 500, 100, 50 and 10 ng/mL.

Example 1

Influence of pH on Measured Value of Cytochrome c in Human Serum

Human cytochrome c diluted in a buffer solution to 30, 100, 500 and 1000 ng/mL (antigen 1, antigen 2, antigen 3, antigen 4), serum 1, serum 2 and serum 3 were added in a volume of 20 μL to 200 μL of an acidic specimen diluent (0.1 M citrate phosphate buffer solution (pH 4.0) containing 0.15 M NaCl, 15 mM EDTA, 5% N102 (NOF Corporation) and 0.1% $NaN_3$) or a neutral specimen diluent (0.1 M citrate phosphate buffer solution (pH 7.5) containing 0.15 M NaCl, 15 mM EDTA, 5% N102 (NOF Corporation) and 0.1% $NaN_3$).

The following measurement was performed by using an electrochemiluminescent enzyme immunoassay reader, Picolumi® 8220 (Sanko Junyaku Co., Ltd.).

The anti-cytochrome c antibody-immobilized beads adjusted to a bead concentration of 1 mg/mL with 0.15 M PBS (pH 7.5) containing 1% BSA, 0.3% sucrose, 0.01% by volume Tween 20 and 0.1% $NaN_3$ were added in a volume of 25 μL to each specimen, and allowed to react for 9 minutes, and the beads were washed twice with 350 μL of Picolumi® BF washing solution (Sanko Junyaku Co., Ltd.). Then, to the beads was added 200 μL of the ruthenium complex-labeled anti-cytochrome c antibody adjusted to a concentration of 0.5 to 1 μg/mL with 0.15 M PBS (pH 7.5) containing 1% BSA, 0.3% sucrose, 0.01 volume % Tween 20 and 0.1% $NaN_3$, and allowed to react for 9 minutes. The beads were washed twice with 350 μL of Picolumi® BF washing solution, 300 μL of Picolumi® luminescent electrolyte (Sanko Junyaku Co., Ltd.) was added to the beads, and luminescence count was measured.

A standard curve was created by plotting the concentration of the standard human cytochrome c antigen on the horizontal axis and the count for the human standard cytochrome c antigen on the vertical axis, and the amounts of cytochrome c contained in antigen 1, antigen 2, antigen 3, antigen 4, serum 1, serum 2 and serum 3 were calculated from the luminescence counts thereof on the basis of the standard curve.

Then, 10 μL each of an antigen and an antigen, or an antigen and a serum were mixed, and 200 μL of the acidic specimen diluent or neutral specimen diluent was similarly added to the mixture, the amount of cytochrome c was obtained by electrochemiluminescent enzyme immunoassay, and the recovery rate was obtained by comparing the actual measured value and the theoretical value. The results obtained by using the anti-cytochrome c monoclonal antibody, 6H2.B4 antibody, immobilized on the beads, and the anti-cytochrome c IgG F(ab')$_2$ polyclonal antibody for the ruthenium complex-labeled antibody are shown in Table 1. The results obtained by using the 2B5F8 monoclonal antibody immobilized on the beads, and the 27G9 monoclonal antibody for the ruthenium complex-labeled antibody are shown in Table 2.

It was revealed that, whichever antibody system was used, when an antigen alone was used, a recovery rate close to 100% was obtained irrespective of pH, whereas when serum was added, the recovery rate decreased to about 2 to 20% at pH 7.5, and the recovery rate recovered to 100% at pH 4.

Further, it was confirmed that whichever combination of antibodies was used, measurement sensitivity in a buffer solution of pH 4 was 1 ng/mL or higher, and thus it was demonstrated that this condition satisfied the requirements for both sensitivity and recovery rate.

TABLE 1

6H2.B4-Poly antibody
pH 7.5
Quantified amount of cytochrome c
(ng/mL)

| | |
|---|---|
| Antigen 1 | 28.8 |
| Antigen 2 | 122.5 |
| Antigen 3 | 623.5 |
| Antigen 4 | 811.9 |
| Serum 1 | 2.6 |
| Serum 2 | 4.5 |
| Serum 3 | 13.6 |

| Combination of antigens | | Measured value | Theoretical value | Recovery rate |
|---|---|---|---|---|
| (A) | (B) | (C) | (D) = ((A) + (B))/2 | (C)/(D) |
| Antigen 1 | Antigen 2 | 73.4 | 75.7 | 97.0% |
| Antigen 3 | Antigen 4 | 748.9 | 717.7 | 104.3% |
| Antigen 2 | Serum 3 | 13.6 | 68.1 | 20.0% |
| Antigen 1 | Serum 2 | 4.0 | 16.7 | 24.0% |
| Antigen 4 | Serum 1 | 113.5 | 407.3 | 27.9% |

6H2.B4-Poly antibody
pH 4
Quantified amount of cytochrome c
(ng/mL)

| | |
|---|---|
| Antigen 1 | 29.6 |
| Antigen 2 | 113.8 |
| Antigen 3 | 616.8 |
| Antigen 4 | 850.9 |
| Serum 1 | 29.0 |
| Serum 2 | 46.6 |
| Serum 3 | 106.1 |

| Combination of antigens | | Measured value | Theoretical value | Recovery rate |
|---|---|---|---|---|
| (A) | (B) | (C) | (D) = ((A) + (B))/2 | (C)/(D) |
| Antigen 1 | Antigen 2 | 68.0 | 71.7 | 94.8% |
| Antigen 3 | Antigen 4 | 750.1 | 733.9 | 102.2% |
| Antigen 2 | Serum 3 | 111.9 | 110.0 | 101.8% |
| Antigen 1 | Serum 2 | 35.0 | 38.1 | 91.9% |
| Antigen 4 | Serum 1 | 535.0 | 440.0 | 121.6% |

TABLE 2

2B5F8-27G9 antibody
pH 7.5
Quantified amount of cytochrome c
(ng/mL)

| | |
|---|---|
| Antigen 1 | 30.2 |
| Antigen 2 | 123.3 |
| Antigen 3 | 587.7 |
| Antigen 4 | 842.5 |
| Serum 1 | 0.3 |
| Serum 2 | 0.6 |
| Serum 3 | 2.3 |

| Combination of antigens | | Measured value | Theoretical value | Recovery rate |
|---|---|---|---|---|
| (A) | (B) | (C) | (D) = ((A) + (B))/2 | (C)/(D) |
| Antigen 1 | Antigen 2 | 80.2 | 76.8 | 104.5% |
| Antigen 3 | Antigen 4 | 761.5 | 715.1 | 106.5% |
| Antigen 2 | Serum 3 | 2.2 | 62.8 | 3.5% |
| Antigen 1 | Serum 2 | 0.3 | 15.4 | 1.9% |
| Antigen 4 | Serum 1 | 35.9 | 421.4 | 8.5% |

2B5F8-27G9 antibody
pH 4
Quantified amount of cytochrome c
(ng/mL)

| | |
|---|---|
| Antigen 1 | 29.2 |
| Antigen 2 | 122.1 |
| Antigen 3 | 595.5 |
| Antigen 4 | 861.5 |
| Serum 1 | 19.1 |
| Serum 2 | 29.9 |
| Serum 3 | 65.4 |

| Combination of antigens | | Measured value | Theoretical value | Recovery rate |
|---|---|---|---|---|
| (A) | (B) | (C) | (D) = ((A) + (B))/2 | (C)/(D) |
| Antigen 1 | Antigen 2 | 81.8 | 75.7 | 108.1% |
| Antigen 3 | Antigen 4 | 761.4 | 728.5 | 104.5% |
| Antigen 2 | Serum 3 | 101.7 | 93.8 | 108.5% |
| Antigen 1 | Serum 2 | 32.6 | 29.6 | 110.3% |
| Antigen 4 | Serum 1 | 468.7 | 440.3 | 106.5% |

Example 2

Measurement of Cytochrome c in Human Serum Using Succinate Buffer Solution

Cytochrome c in human serum was measured by using a succinate buffer solution instead of a citrate phosphate buffer solution.

To 200 μL of a specimen diluent (0.1 M succinic acid, 0.15 M NaCl, 2% Lipidure BL802 (NOF Corporation), 2% Lipidure BL405 (NOF Corporation), 15 mM EDTA.2Na, 0.1% NaN$_3$, pH 4.0), 20 μL each of human cytochrome c diluted in a buffer solution (0.05 M Tris-HCl, pH 7.8, 5% BSA, 0.15 M NaCl, 0.1% NaN$_3$) to 5, 10, 100, 1000 and 3000 ng/mL (antigen 1, antigen 2, antigen 3, antigen 4, antigen 5), serum 1, serum 2, serum 3 and serum 4 were added.

The following measurement was performed by using an electrochemiluminescent enzyme immunoassay reader, Picolumi® 8220 (Sanko Junyaku Co., Ltd.).

To each specimen, 25 μL of the anti-cytochrome c antibody-immobilized beads adjusted to a bead concentration of 1 mg/mL with 0.05 M Tris-HCl (pH 7.5) containing 1% BSA, 0.15 M NaCl, 0.3% trehalose, 0.01 volume % volume Tween 20, 10 mM EDTA.2Na, 25 μg/mL mouse IgG and 0.1% NaN$_3$ was added, and allowed to react for 9 minutes. The beads were washed twice with 350 μL of Picolumi® BF washing solution (Sanko Junyaku Co., Ltd.), and to the beads was added 200 μL of the ruthenium complex-labeled anti-cytochrome c antibody adjusted to a concentration of 1 μg/mL with 0.05 M Tris-HCl (Ph 7.5) containing 1% BSA, 0.15 M NaCl, 0.3% trehalose, 0.01 volume % Tween 20 and 0.3% NaN$_3$, and allowed to react for 9 minutes. The beads were washed twice with 350 μL of Picolumi® BF washing solution, 300 μL of Picolumi® luminescent electrolyte (Sanko Junyaku Co., Ltd.) was added to the beads, and luminescence count was measured.

A standard curve was created by plotting the concentration of the standard human cytochrome c antigen on the horizontal axis and the count of the standard human cytochrome c antigen on the vertical axis, and the amounts of cytochrome c contained in antigen 1, antigen 2, antigen 3, antigen 4, antigen 5, serum 1, serum 2, serum 3 and serum 4 were obtained from the luminescence counts thereof by using the standard curve.

The results obtained by using an anti-cytochrome c monoclonal antibody, the 2B5F8 antibody, immobilized on the beads, and the anti-cytochrome 27G9 monoclonal antibody or the 6H2.B4 monoclonal antibody for the ruthenium complex-labeled antibody are shown in Table 3. When this reagent was used, it was confirmed that the recovery rate was also 100%, and the measurement sensitivity was 1 ng/mL or higher. Thus, it was demonstrated that this condition also satisfied the requirements for both sensitivity and recovery rate.

TABLE 3

2B5F8-27G9 antibody
Quantified amount of cytochrome c
(ng/mL)

| | |
|---|---|
| Antigen 1 | 5.0 |
| Antigen 2 | 10.2 |
| Antigen 3 | 97.1 |
| Antigen 4 | 1033.2 |
| Antigen 5 | 2927.1 |
| Serum 1 | 21.9 |
| Serum 2 | 76.5 |
| Serum 3 | 511.9 |
| Serum 4 | 1452.9 |

| Combination of antigens | | Measured value | Theoretical value | Recovery rate |
|---|---|---|---|---|
| (A) | (B) | (C) | (D) = ((A) + (B))/2 | (C)/(D) |
| Antigen 1 | Serum 1 | 14.7 | 13.5 | 109.3% |
| Antigen 2 | Serum 1 | 16.5 | 16.1 | 102.8% |
| Antigen 2 | Serum 2 | 46.3 | 43.4 | 106.8% |
| Antigen 3 | Serum 2 | 86.6 | 86.8 | 99.8% |
| Antigen 3 | Serum 3 | 331.6 | 304.5 | 108.9% |
| Antigen 4 | Serum 3 | 740.5 | 722.6 | 95.9% |
| Antigen 4 | Serum 4 | 1205.4 | 1243.1 | 97.0% |
| Antigen 5 | Serum 4 | 2195.7 | 2190.0 | 100.3% |

2B5F8-6H2.B4 antibody
Quantified amount of cytochrome c
(ng/mL)

| | |
|---|---|
| Antigen 1 | 4.6 |
| Antigen 2 | 9.2 |
| Antigen 3 | 108.3 |
| Antigen 4 | 1090.0 |
| Antigen 5 | 2859.8 |
| Serum 1 | 20.1 |
| Serum 2 | 76.4 |
| Serum 3 | 541.0 |
| Serum 4 | 1463.4 |

| Combination of antigens | | Measured value | Theoretical value | Recovery rate |
|---|---|---|---|---|
| (A) | (B) | (C) | (D) = ((A) + (B))/2 | (C)/(D) |
| Antigen 1 | Serum 1 | 12.1 | 12.4 | 98.0% |
| Antigen 2 | Serum 1 | 14.3 | 14.7 | 97.6% |
| Antigen 2 | Serum 2 | 44.9 | 42.8 | 104.9% |
| Antigen 3 | Serum 2 | 91.8 | 92.4 | 99.4% |
| Antigen 3 | Serum 3 | 370.3 | 324.7 | 114.1% |
| Antigen 4 | Serum 3 | 794.4 | 815.5 | 97.4% |
| Antigen 4 | Serum 4 | 1339.8 | 1276.7 | 104.9% |
| Antigen 5 | Serum 4 | 2072.1 | 2161.6 | 95.9% |

Example 3

Identification of Interference Substances Inhibiting Accurate Measurement of Cytochrome c in Human Serum (1) Gel Filtration of Human Serum Human serum in a volume of 2 mL was subjected to gel filtration based on gel chromatography using a Sephacryl S-200 (GE HEALTHCARE Biosciences) column (size φ 2.5 cm×120 cm) and PBS as an eluent to collect about 7-mL fractions. To 0.5 mL of each fraction was added 50 μL of human cytochrome c (R&D Systems) dissolved in purified water at a concentration of 10 μg/mL, and mixed, and 50 μL of the mixture was diluted with 50 μL of a solution for reaction (0.15 M PBS, 15 mM EDTA, 1% BSA, 0.1% $NaN_3$, pH 7.5). On an automatic electrochemiluminescent enzyme immunoassay reader, Picolumi® 8220 (Sanko Junyaku Co., Ltd.), the anti-cytochrome c antibody (2B5F8)-bound beads prepared in the reference example, ruthenium complex-labeled anti-cytochrome c antibody (3G7) prepared in the reference example and diluted with 0.15 M PBS (pH 7.5) containing 1% BSA, 0.3% sucrose, 0.01 volume % Tween 20 and 0.1% $NaN_3$ to 2 μg/mL, Picolumi® luminescent electrolyte (Sanko Junyaku Co., Ltd.), Picolumi® BF washing solution (Sanko Junyaku Co., Ltd.), Picolumi® cell cleaner solution (Sanko Junyaku Co., Ltd.) and Picolumi® nozzle rinsing solution (Sanko Junyaku Co., Ltd.) were set, and the measurement was performed under conditions of an anti-cytochrome c antibody-bound bead volume of 25 μL, ruthenium-labeled anti-cytochrome c antibody volume of 100 μL, Picolumi® luminescent electrolyte volume of 300 μL, 1 step and a reaction time of 26 minutes.

As a result, the luminescence count decreased around the fraction No. 41. Therefore, it was found that the fraction No. 41 contained interference substances that inhibited the reaction of cytochrome c and the anti-cytochrome c antibody (FIG. 1).

(2) Identification of Fraction Containing Interference Substances by Two-dimensional Electrophoresis and Mass Spectrometry With reference to the method described in Hiroyuki Katayama et al., Optimization of in-gel protein digestion system in combination with thin-gel separation and negative staining in 96-well plate format: Rapid Commun. in Mass Spectrom., 2003, 17:1071-1078, the fraction containing interference substances was separated by two-dimensional electrophoresis, and each spot was identified by mass spectrometry (proteome technique).

The gel filtration fraction No. 41 in a volume of 0.5 mL was subjected to an albumin elimination treatment using Swell Gel® Blue Albumin Removal Kit (PIERCE). Then, to perform two-dimensional electrophoresis, 0.44 mL of a swelling buffer solution (8 M urea, 2% CHAPS, 0.5% IPG Buffer, bromophenol blue, 0.6% dithiothreitol) and 0.11 mL of the gel filtration fraction from which albumin was eliminated were mixed, and a gel for isoelectric focusing electrophoresis, Immobilize Dry Strip pH3-10, 18 cm (GE HEALTH-CARE Biosciences), was immersed in the mixture and left at room temperature overnight to swell the gel. The gel was set on Cool Phore Star IPG-IEF Type-P (Anatech) and subjected to electrophoresis at voltages of 500 V 2 h, 700 V 1 h, 1000 V 1 h, 1500 V 1 h, 2000 V 1 h, 2500 V 1 h, 3000 V 1 h and 3500 V 10 h~applied by Power Phore Star Pro (Anatech). The gel subjected to electrophoresis was immersed in an SDS treatment buffer solution (50 mM Tris-HCl, pH 6.8, 6 M urea, 0.25% dithiothreitol, 2% SDS, 0.0025% bromophenol blue, 30 volume % glycerol), the buffer solution was stirred at room temperature for 10 minutes, then the gel was immersed in a reduction alkylation buffer solution (50 mM Tris-HCl, pH 6.8, 6 M urea, 2% SDS, 0.0025% bromophenol blue, 30 volume % glycerol, 4.5% iodoacetamide), the buffer solution was stirred at room temperature for 10 minutes, and loaded on to 2D Quick Gel (Anatech), and electrophoresis was performed. The gel was subjected to electrophoresis was stained with Coomassie brilliant blue, and the spots were excised with a cutter.

Each excised gel was finely cut with a cutter, and put into a tube, 100 μL of a mixture of 50 mM $NH_4HCO_3$ and acetonitrile (1:1) was injected to the tube, and the mixture was stirred at room temperature for 60 minutes. The mixture of 50 mM $NH_4HCO_3$ and acetonitrile (1:1) was renewed, and further stirred at room temperature for 40 minutes to decolorize Coomassie brilliant blue.

The mixture was replaced with 100 μL of a washing solution (50% methanol, 10% acetic acid, 40% purified water), and the mixture containing the gel was temporarily stored at 4° C. The washing solution was removed, and the gel was washed three times with 100 μL/tube of a mixture of 50 mM $NH_4HCO_3$ and acetonitrile (1:1). Then, 100 μL/tube of 100 mM $NH_4HCO_3$ was added, and the mixture was stirred at room temperature for 5 minutes. The solution was removed, and 100 μL/tube of 100 mM $NH_4HCO_3$ containing 2.5 mg/mL of DTT was added, and the mixture was stirred for 15 minutes. The solution was removed, and 100 μL/tube of 100 mM $NH_4HCO_3$ containing 45 mg/mL of acrylamide was added, and the mixture was stirred for 15 minutes. The solution was removed, and 500 μL/tube of a mixture of methanol, acetic acid and purified water (5:1:4) was added, and the mixture was stirred at room temperature for 16 hours. The solution was renewed, and the mixture was further stirred at room temperature for 30 minutes. The solution was removed, and 500 μL/tube of 50 mM $NH_4HCO_3$ was added, and the mixture was stirred at room temperature for 10 minutes. The solution was removed, and 500 μL/tube of acetonitrile was added, and the mixture was stirred at room temperature for 5 minutes.

The lid of the tube was opened, the tube was set on a vacuum centrifugal drier (Tomy Seiko Co., Ltd., SpeedVac), and the mixture was dried under reduced pressure until the mixture solidified. Then, 2.5 μL of a solution obtained by adding 5 μL of 200 μg/mL trypsin to 45 μL of a mixture of 0.2% n-octylglucoside (Sigma) and 50 mM $NH_4HCO_3$ (1:1) was taken, added to the dried gel, and allowed to react at room temperature for 5 minutes. To the reaction mixture was added 8 μL of a mixture of 50 mM $NH_4HCO_3$ and 0.2% n-octylglucoside (1:1), and the mixture was left at 37° C. for 16 hours. To the mixture was added 40 μL of 50% acetonitrile containing 0.1% TFA, and the mixture was treated in an ultrasonic water tank for 10 minutes. The solution was transferred to another tube, to the remaining gel was added 40 μL of 75% acetonitrile containing 0.1% TFA, and the mixture was treated in the ultrasonic water tank for 10 minutes. The solution was collected, and mixed with the solution previously transferred to another tube. Then, the combined solution was dried with a vacuum freeze dryer.

To the dried sample was added 50 μL of 5% acetonitrile containing 0.1% TFA, and the mixture was stirred to dissolve the sample. The whole volume of the dissolved sample was applied to a column in which a gel for C18 reverse phase chromatography was packed and washed twice with 200 μL and 50 μL of methanol beforehand. The column was subjected to centrifugation at 2000 rpm for 5 minutes to completely flow the applied sample. Then, 50 μL of 5% acetonitrile containing 0.1% TFA was added to the column, and the column was subjected to centrifugation at 2000 rpm for 5 minutes for washing. This washing was repeated three times. Then, 25 μL of 95% acetonitrile containing 0.1% TFA was added to the column, and the column was subjected to centrifugation at 2000 rpm for 5 minutes to elute the sample. The eluted solution was left at 37° C. for drying.

Figure 2:
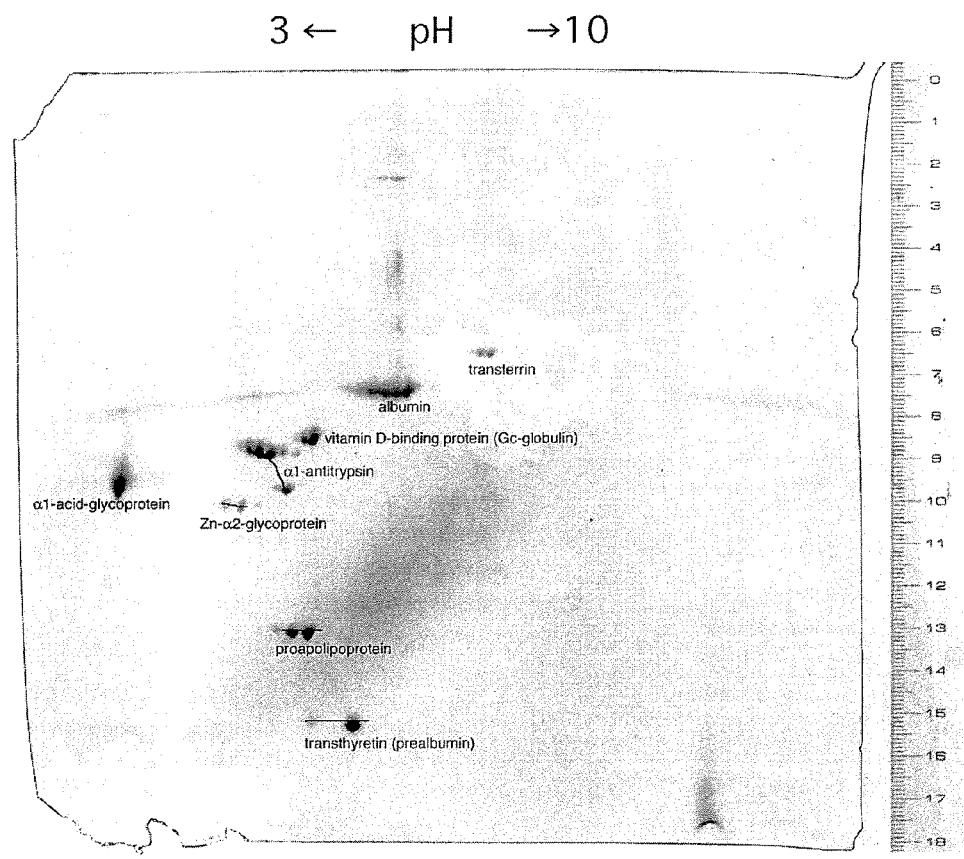
FIG. 2 shows results of two-dimensional electrophoresis of a fraction containing interference substances (electrophoresis photograph). Names of the identified proteins are appended to the spots.

The sample was dissolved in 5% acetonitrile containing 0.1% TFA in a tube and subjected to mass spectrometry with LC-MASS Analyzer (Thermo Electron Co., Ltd., LCQ) to identify the spots obtained in the two-dimensional electrophoresis. The results are shown in FIG. 2.

(3) Influence of Identified Proteins on Measurement of Cytochrome c

Among the identified proteins, those marketed and available except for albumin were added to the cytochrome c measurement system to measure cytochrome c and thereby examine whether they had interference activity.

1) Human transferrin (Biogenesis) in an amount of 6.5 mg was dissolved in 0.65 mL of purified water to prepare 10 mg/mL of transferrin solution.
2) Human α1-acid glycoprotein (Athens Research & Technology) in an amount of 1 mg was dissolved in 0.5 mL of PBS-1 to obtain an α1-acid glycoprotein solution.
3) Human α1-antitrypsin (CALBIOCHEM) in an amount of 1 mg was dissolved in 0.33 mL of purified water to obtain an α1 antitrypsin solution.
4) Human transthyretin (prealbumin, Sigma) in an amount of 1 mg was dissolved in 0.3 mL of a 50 mM phosphate buffer solution (pH 7.5) containing 0.15 M NaCl to obtain a transthyretin solution.
5) Human vitamin D-binding protein (Gc-globulin, CALBIOCHEM) in an amount of 1 mg was dissolved in 0.5 mL of purified water to obtain a vitamin D-binding protein solution.

To 100 μL of a solution for reaction (0.15 M PBS, 15 mM EDTA, 1% BSA, 0.1% $NaN_3$, pH 7.5) were added 0 or 10 μL of the solution of each identified protein and 1 μL of human cytochrome c (10 μg/mL). On an automatic electrochemiluminescent enzyme immunoassay reader, Picolumi® 8220 (Sanko Junyaku Co., Ltd.), the anti-cytochrome c antibody (2B5F8)-bound beads, the ruthenium complex-labeled anti-cytochrome c antibody (27G9), which were prepared in the reference examples, Picolumi® luminescent electrolyte (Sanko Junyaku Co., Ltd.), Picolumi® BF washing solution (Sanko Junyaku Co., Ltd.), Picolumi® cell cleaner solution (Sanko Junyaku Co., Ltd.) and Picolumi® nozzle rinsing solution (Sanko Junyaku Co., Ltd.) were set, and the measurement was performed under conditions of an anti-cytochrome c antibody-bound bead volume of 25 μL, ruthenium-labeled anti-cytochrome c antibody volume of 100 μL, Picolumi® luminescent electrolyte volume of 300 μL, 1 step and a reaction time of 26 minutes. As a result, decrease in the spiked recovery rate was observed with the α1-acid glycoprotein and α1-antitrypsin, and thus it was found that they had an interference activity (Table 4).

TABLE 4

| Identified protein | Spiked recovery rate (% based on control) |
|---|---|
| Transferrin | 99% |
| α1-Acid glycoprotein | 40% |
| α1-Antitrypsin | 58% |
| Transthyretin | 100% |
| Vitamin D-binding protein | 93% |

(4) Influence of Identified Interference Substances on Measurement of Cytochrome c in Acidic Range The measurement was performed according to the measurement method under the following acidic condition or neutral condition as the reaction condition.

1) Acidic Condition
    Acidic solution for reaction (0.05 M citric acid, 1% BSA, 0.15 M NaCl, 15 mM EDTA, pH 4.0)
    Ruthenium diluent (0.05 M citric acid, 1% BSA, 0.15 M NaCl, 0.3% sucrose, 0.01% Tween 20, pH 4.0)
2) Neutral Condition
    Neutral solution for reaction (0.15 M PBS, 15 mM EDTA, 1% BSA, 0.1% $NaN_3$, pH 7.5)
    Ruthenium diluent (0.15 M PBS, 1% BSA, 0.3% sucrose, 0.01% Tween 20, 0.1% $NaN_3$, pH 7.5)
3) Measurement Method To 100 μL of a solution for reaction was added 10 μL of a solution of a protein found to have an interference activity, i.e., α1-acid glycoprotein solution (2 mg/mL) or α1-antitrypsin solution (3 mg/mL), and 1 μL of a solution of human cytochrome c (R&D Systems) dissolved in purified water at a concentration of 10 μg/mL, and mixed. Together with this mixture, on an automatic electrochemiluminescent enzyme immunoassay reader, Picolumi® 8220 (Sanko Junyaku Co., Ltd.), the anti-cytochrome c antibody (2B5F8)-bound beads prepared in the reference example, the ruthenium-labeled anti-cytochrome c antibody (3G7) prepared in the reference example and diluted with the ruthenium diluent, Picolumi® luminescent electrolyte (Sanko Junyaku Co., Ltd.), Picolumi® BF washing solution (Sanko Junyaku Co., Ltd.), Picolumi® cell cleaner solution (Sanko Junyaku Co., Ltd.), and Picolumi® nozzle rinsing solution (Sanko Junyaku Co., Ltd.) were set, and the measurement was performed under conditions of an anti-cytochrome c antibody-bound bead volume of 25 μL, ruthenium-labeled anti-cytochrome c antibody volume of 100 μL, Picolumi® luminescent electrolyte volume of 300 μL, 1 step and a reaction time of 26 minutes.

As a result, as shown in Table 5, it was revealed that the interference activity could be avoided by lowering pH at the time of the antigen-antibody reaction as in the measurement with human serum.

Both the substances having the interference activity are highly acidic proteins, and it is considered that interaction of these highly acidic proteins with highly basic cytochrome c influenced on the measurement of cytochrome c. It appears that, since the interaction between cytochrome c and an interference substance became weaker in the measurement in an acidic range, accurate quantification was enabled in the acidic range. Therefore, it is expected that accurate quantification of cytochrome c would also be enabled in an acidic range with antibodies other than those investigated in the examples.

TABLE 5

| | Spiked recovery rate | |
|---|---|---|
| | pH 4.0 | pH 7.5 |
| Control | 100.0% | 100.0% |
| α1-Acid glycoprotein | 99.8% | 66.7% |
| α1-Antitrypsin | 99.2% | 74.0% |

INDUSTRIAL APPLICABILITY

Cytochrome c in a body fluid is known to serve as an index of apoptosis occurring in the body and has been found to be effective as a diagnostic agent for many diseases. More accurate measurement of cytochrome c amount is enabled by the immunochemical measurement method for cytochrome c of the present invention using a buffer solution in an acidic range, and application of this method to diagnostic agents is expected.

What is claimed is:

1. A method for immunochemically measuring cytochrome c in a body fluid, which comprises reacting an antibody and cytochrome c in an acidic buffer solution; and measuring the binding of the antibody and cytochrome c to determine the amount of cytochrome c in the body fluid.

2. The method according to claim 1, wherein the acidic buffer solution has a pH of 3.5 to 5.0.

3. The method according to claim 1, wherein the body fluid is blood.

4. A kit for immunochemically measuring cytochrome c in a body fluid, comprising an antibody that reacts with cytochrome c; and an acidic buffer solution suitable for reacting the antibody and cytochrome c.

5. The kit according to claim 4, wherein the acidic buffer has a pH of 3.5 to 5.0.

6. The kit according to claim 4, wherein the antibody is immobilized or labeled.

7. The method according to claim 2, wherein the body fluid is blood.

8. The kit according to claim 5, wherein the antibody is immobilized or labeled.

9. The method according to claim 1, wherein the antibody is immobilized or labeled.

10. The method according to claim 1, wherein the acidic buffer has a pH of 3.5 to 4.5.

11. The kid according to claim 4, wherein the acidic buffer has a pH of 3.5 to 4.5.

* * * * *